(12) United States Patent
McLeod

(10) Patent No.: US 10,092,689 B2
(45) Date of Patent: Oct. 9, 2018

(54) INTRAVENOUS MEDICAMENT LINE ORGANIZER

(71) Applicant: Eric McLeod, Austin, TX (US)

(72) Inventor: Eric McLeod, Austin, TX (US)

(73) Assignee: Eric McLeod, Nashville, TN (US)

( * ) Notice: Subject to any disclaimer, the term of this patent is extended or adjusted under 35 U.S.C. 154(b) by 0 days.

(21) Appl. No.: 15/160,644

(22) Filed: May 20, 2016

(65) Prior Publication Data

US 2016/0346461 A1  Dec. 1, 2016

Related U.S. Application Data

(60) Provisional application No. 62/165,305, filed on May 22, 2015.

(51) Int. Cl.
*A61M 5/14* (2006.01)
*A61M 5/142* (2006.01)
*F16L 3/22* (2006.01)

(52) U.S. Cl.
CPC .......... *A61M 5/1418* (2013.01); *A61M 5/142* (2013.01); *A61M 5/1408* (2013.01); *A61M 5/1413* (2013.01)

(58) Field of Classification Search
CPC .. A61M 5/1418; A61M 5/1408; A61M 5/142; A61M 5/1413
See application file for complete search history.

(56) References Cited

U.S. PATENT DOCUMENTS

| | | | | |
|---|---|---|---|---|
| 4,406,042 A | * | 9/1983 | McPhee | A61M 5/1418 24/129 A |
| 6,105,218 A | * | 8/2000 | Reekie | A61M 5/1418 24/115 R |
| 6,323,430 B1 | * | 11/2001 | Finona | H01R 9/0518 174/135 |
| 9,387,303 B2 | * | 7/2016 | Pittaway | A61M 5/1418 |
| 2006/0047268 A1 | * | 3/2006 | Stephens | A61M 5/1418 604/533 |
| 2014/0152000 A1 | * | 6/2014 | Chen | F16L 3/237 285/124.1 |
| 2014/0243625 A1 | * | 8/2014 | Warren | A61M 5/16836 600/310 |

* cited by examiner

*Primary Examiner* — Robert Sandy
*Assistant Examiner* — Louis A Mercado
(74) *Attorney, Agent, or Firm* — Miller Canfield

(57) ABSTRACT

An intravenous line organizer for organizing a plurality of intravenous lines, each being interconnected with a medicament pump is disclosed. A plurality of holders is defined by an elongated tubular wall defining an axis, with adjacent of the tubular walls having parallel axis and being interconnected by a joining member. Each of the tubular walls defines an entry way for receiving an intravenous line used for delivering medicament to a patient. The entry way includes mating appendages for retaining the intravenous line within the holder.

8 Claims, 3 Drawing Sheets

INTRAVENOUS MEDICAMENT LINE ORGANIZER

PRIOR APPLICATIONS

The present application claims priority to U.S. Provisional Patent Application No. 62/165,305 filed May 22, 2015, the contents of which are incorporated herein by reference.

TECHNICAL FIELD

The present invention relates generally toward improving delivery of medicament to a patient. More specifically, the present invention relates toward an organizer for intravenous lines for delivering intravenous medicaments to a patient.

BACKGROUND

Medicaments have been delivered intravenously to patients for many years. In fact, it is quite common to deliver multiple medicaments intravenously at the same time. In many intensive care units of hospitals, it is common to have four or more medicaments delivered intravenously. In fact, after some complicated surgeries up to 16 different medicaments are delivered intravenously to a patient.

Quite often, these medicaments are delivered into a single intravenous needle inserted into the jugular vein or other large artery of a patient. When a patient is being moved, or, otherwise moves on his or her own accord, these intravenous lines are known to become entangled making it difficult to determine which line leads to which medicament. On occasion, a given line can become blocked for a variety of reasons. When upwards of 16 medicament lines are entangled, it is difficult to determine which of these lines are not delivering a proper amount of medicament. Therefore, it would be desirable to provide a cost effective manner in which to organize these lines to prevent known entanglements from occurring to the detriment of the patient.

SUMMARY

An intravenous line organizer for organizing a plurality of intravenous lines that are interconnected with a medicament pump, or individual medicament pumps, is disclosed. The line organizer includes a plurality of holders that are each defined by an elongated tubular wall. Each tubular wall defines an axis with adjacent of the tubular walls defining parallel axis. The tubular walls are interconnected with a joining member, also extending parallel to the axis defined by the tubular walls. Each of the tubular walls defines an entryway for receiving an intravenous line for delivering medicament to a patient. The entryway includes mating appendages for retaining the intravenous line within the holder.

The elongated holders of the present invention, for the first time, prevent a full extent of multiple intravenous lines being used simultaneously from becoming entangled.

BRIEF DESCRIPTION OF THE DRAWINGS

Other advantages of the present invention will be readily appreciated, as the same becomes better understood by reference to the following detailed description when considered in connection with the accompanying drawings, wherein.

BACKGROUND

Figure 1:
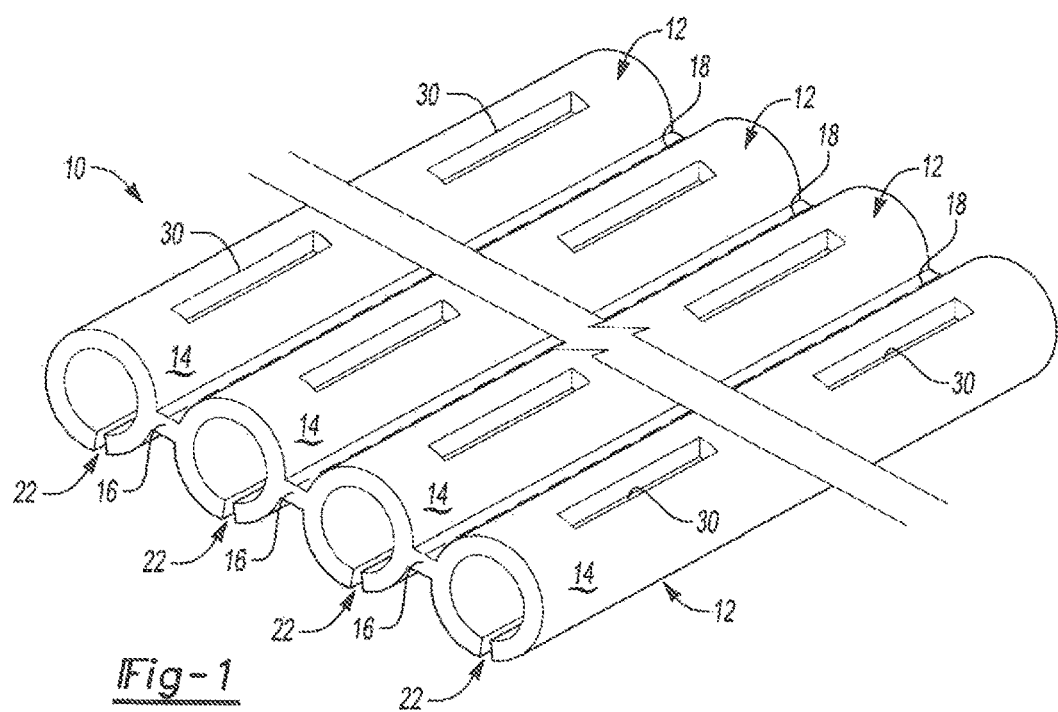
FIG. 1 shows an intravenous medicament line organizer of the present invention.
Figure 2:
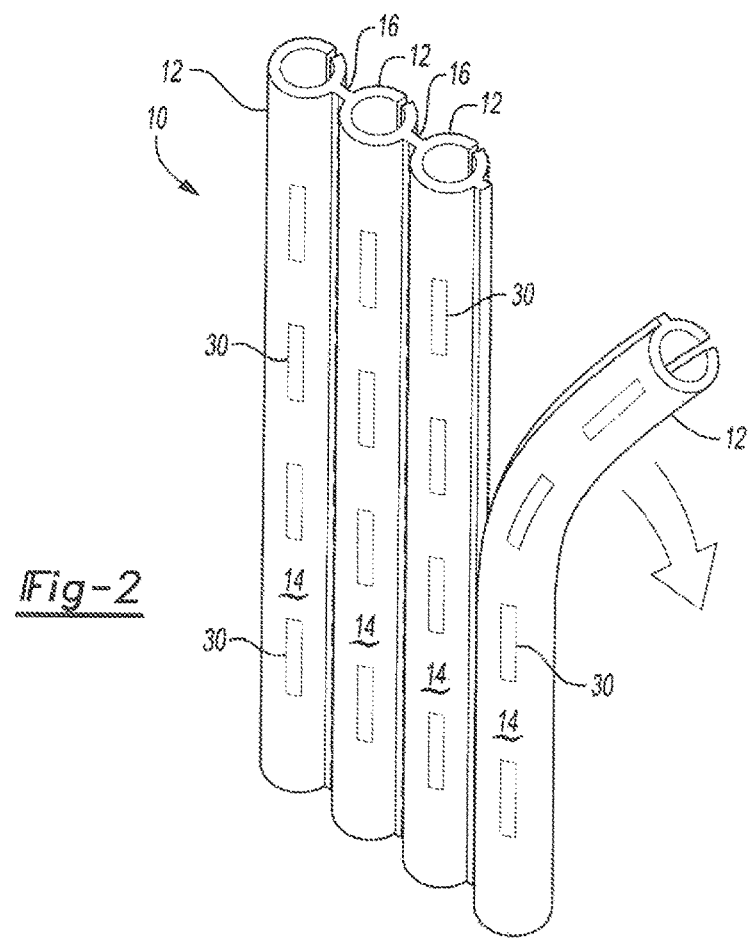
FIG. 2 shows a holder being removed from the intravenous line organizer.
Figure 3:
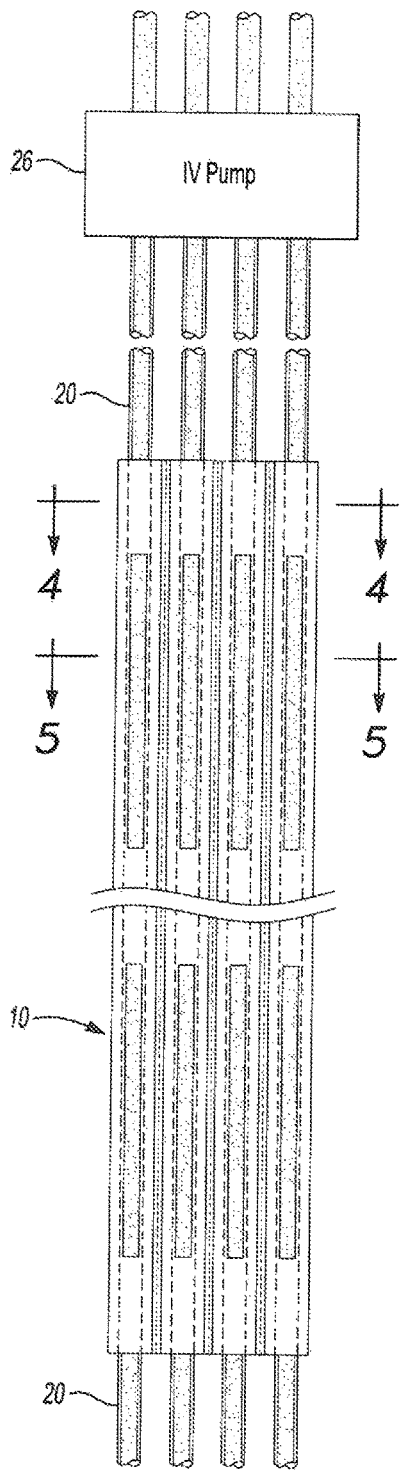
FIG. 3 shows a plan view of intravenous medicament lines disposed within the holders of the line organizer.

Referring to FIG. 1, an intravenous line organizer of the present invention is generally shown at 10. The organizer 10 includes a plurality of holders 12. Each holder 12 is defined by an elongated tubular wall 14. Each tubular wall defines an axis a (best seen in FIGS. 4 and 5) such that adjacent of the tubular walls 14 define parallel axis. Adjacent holders 12 are interconnected by adjoining member 16.

A plurality of holders are each interconnected by adjoining member 16 so that an individual line organizer 10 may include 2, 3, 4 or more parallel holders 12. Therefore, a large number of intravenous lines 20 are maintained in an orderly manner with a single organizer 10.

Perforations 18 are defined by each joining member 16 and extend the full length of the joining member 16. The perforations 18 provide the ability to tear an individual joining member 16 to separate one of the holders 12 from the organizer 10 as represented in FIG. 1. For example, in the instance that only three intravenous lines 20 are used by a particular patient, one of the holders 12 may be removed from an organizer 10 originally having 4 holders 12 to reduce the mass of the organizer 10 as will be explained further herein below.

Figure 4:
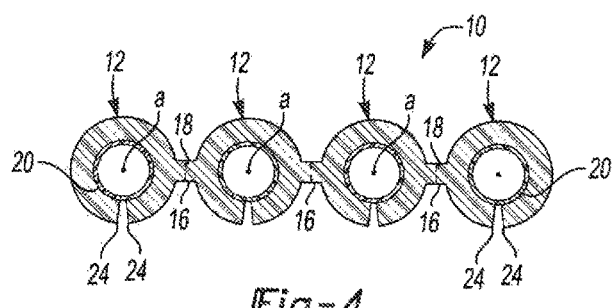
FIG. 4 shows a cross-sectional view of the line organizer through line 4-4 of FIG. 3.
Figure 5:
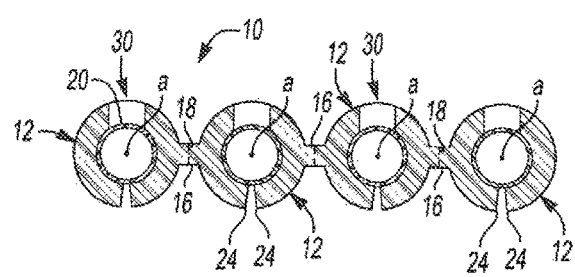
FIG. 5 shows a cross-sectional view of the line organizer through line 5-5 of FIG. 3.
Figure 6:
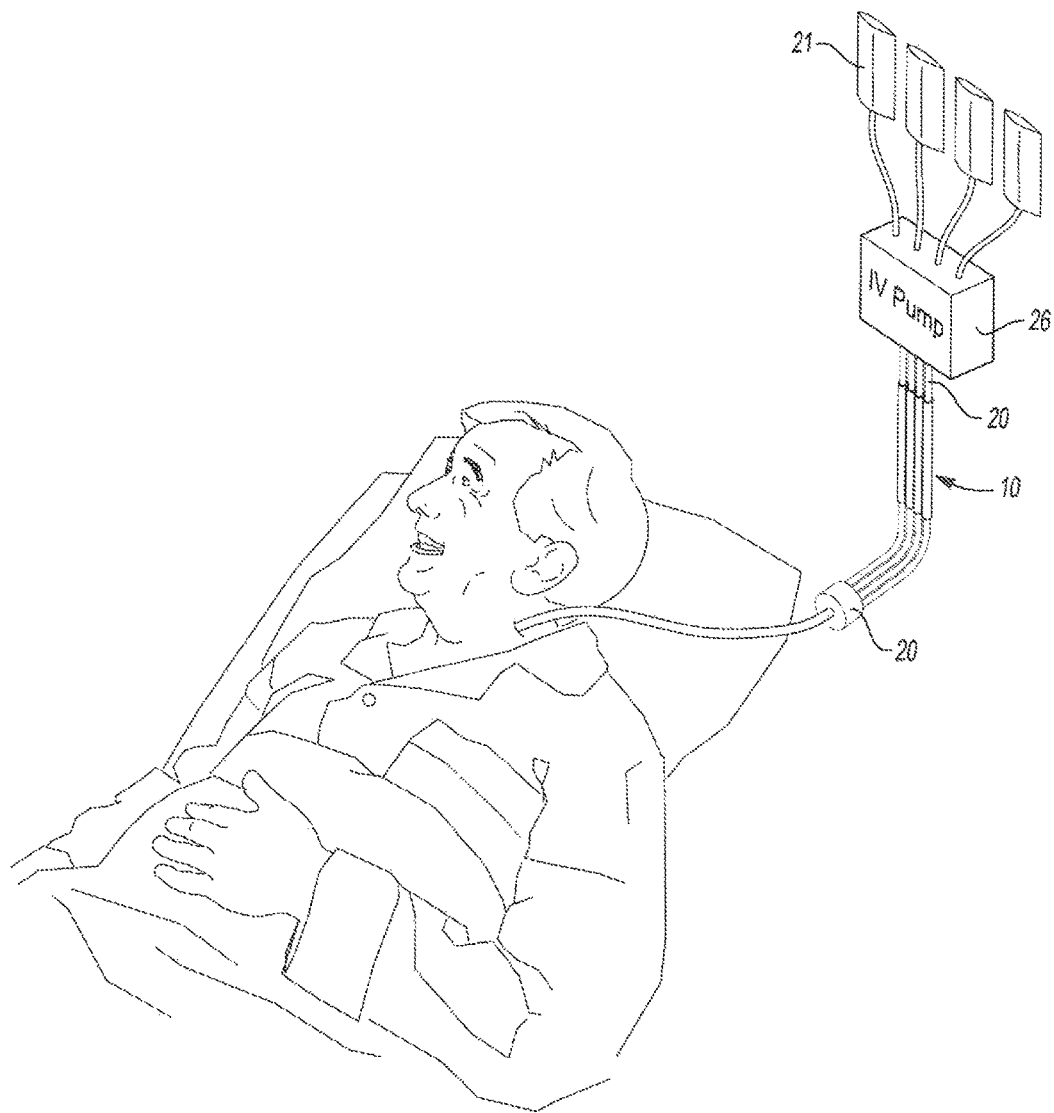
FIG. 6 shows the line organizer of the present invention in use.

Each holder 12 includes an entryway 22 for receiving an intravenous line 20 used to convey medicament disposed in a medicament bag 21 in a known manner. Each entryway 22 is defined by mating appendages 24 as best seen in FIGS. 4 and 5. It should be understood that the tubular wall 14 circumscribes nearly the entire intravenous line disposed with the holder 12. In one embodiment, the organizer 10 extends generally the full length of the intravenous line 20 between an intravenous pump 26 and an intravenous port 28 that is interconnected with an intravenous needle (not shown).

It is contemplated by the inventors that the organizer 10 is formed of a flexomeric polymer so that the holders 12 flex with the intravenous lines 20 when necessary. In one embodiment, the organizer 10 is formed of a nitrile material similar to that of a medical glove to reduce mass of the organizer 10. It is desirable that the organizer 10 does not add a considerable amount of mass to the intravenous lines 20 so that the lines 20 do not weigh down the port 28, which could extract an intravenous needle from a patient. Further, the organizer 10 is less rigid than even the intravenous line 20 disposed therein so that the intravenous lines may flex in a normal manner while still preventing the intravenous lines from becoming entangled.

Each tubular wall 14 defines an opening 30 to provide visual access to the intravenous line 20 disposed within the holder 12. In one embodiment, a plurality of openings 30 is spaced along an entire length of the tubular wall 14. This manner, an observer can identify if a blockage has occurred in any one of the intravenous lines 20 within any of the holders 12. Alternatively, the organizer 10 is formed from a transparent, flexomeric polymer providing visual access to the intravenous lines 20 disposed within each holder 12.

Invention has been described in an illustrative manner, and it is to be understood that the terminology which has been used is intended to be in the nature of words of description rather than of limitation. It is now apparent to those skilled in the art that many modifications and variations of the present invention are possible in light of the above teachings. It is, therefore, to be understood that the invention may be practiced otherwise and is specifically described, and still be within the scope of the present invention.

What is claimed is:

1. An intravenous line organizer for organizing a plurality of intravenous lines, each being interconnected with a medicament pump, comprising:
    a plurality of holders, each holder being defined by an elongated tubular wall defining an axis, with adjacent of said tubular walls having parallel axis and being interconnect with a joining member;
    each of said tubular walls defining an entry way for receiving an intravenous line for delivering medicament patient and said entry way having mating appendages for retaining the intravenous line within said holder; and
    each of said tubular walls define a plurality of openings spaced there along providing visual access to the intravenous line disposed therein.

2. The line organizer set forth in claim 1, wherein each of said tubular walls are formed from a transparent material providing visual access to the intravenous line disposed therein.

3. The line organizer set forth in claim 1, wherein said line organizer is formed from flexomeric polymers providing flexibility to said tubular walls.

4. The line organizer set forth in claim 1, wherein said line organizer extends substantially along a length of an intravenous line.

5. The line organizer set forth in claim 1, wherein the line organizer is less rigid than the intravenous lines disposed therein.

6. The line organizer set forth in claim 1, wherein each holder flexes with the intravenous line disposed therein.

7. An intravenous line organizer for organizing a plurality of intravenous lines, each being interconnected with a medicament pump, comprising:
    a plurality of holders, each holder being defined by an elongated tubular wall defining an axis, with adjacent of said tubular walls having parallel axis and being interconnect with a joining member;
    each of said tubular walls defining an entry way for receiving an intravenous line for delivering medicament patient and said entry way having mating appendages for retaining the intravenous line within said holder; and
    said joining member disposed between adjacent of said tubular walls is perforated thereby allowing adjacent of said tubular walls to be separated.

8. The line organizer set forth in claim 7, wherein
said plurality of holders is defined by at least four holders.

\* \* \* \* \*